US007202394B1

(12) United States Patent
Urade et al.

(10) Patent No.: US 7,202,394 B1
(45) Date of Patent: Apr. 10, 2007

(54) ANIMAL WITH THE MASS EXPRESSION OF HUMAN GENE AND TEST METHOD BY USING THE ANIMAL

(75) Inventors: Yoshihiro Urade, Kyoto (JP); Yasushi Fujitani, Osaka (JP); Hiroaki Kitayama, Kyoto (JP); Naoki Hayashi, Kanagawa (JP)

(73) Assignees: Japan Science and Technology Corporation, Saitama (JP); Osaka Bioscience Institute, Osaka (JP); Oriental Yeast Co., Ltd., Tokyo (JP)

( * ) Notice: Subject to any disclaimer, the term of this patent is extended or adjusted under 35 U.S.C. 154(b) by 79 days.

(21) Appl. No.: 10/089,883

(22) PCT Filed: Oct. 5, 2000

(86) PCT No.: PCT/JP00/06963

§ 371 (c)(1),
(2), (4) Date: Jan. 10, 2003

(87) PCT Pub. No.: WO01/24627

PCT Pub. Date: Apr. 12, 2001

(30) Foreign Application Priority Data

Oct. 5, 1999 (JP) .................................. 11/284610
Jun. 2, 2000 (JP) .............................. 2000/166726

(51) Int. Cl.
*A01K 67/027* (2006.01)
*G01N 33/00* (2006.01)
(52) U.S. Cl. .......................................... 800/18; 800/3
(58) Field of Classification Search .................... 800/3, 800/8, 14, 18
See application file for complete search history.

(56) References Cited

FOREIGN PATENT DOCUMENTS

| JP | 9-322773 | 12/1997 |
| JP | 11-332417 | 12/1999 |

OTHER PUBLICATIONS

Urade (1998) Gene Engineering Studies on Sleep Nippon Rishon 56(2): 488-92.*
Reginato et al (1998) Prostaglandins Promote and Block Adipogenesis through Opposing Effects and Peroxisome Proliferator-activated receptor gamma 273(4): 1855-1858.*
Haberl et al (1998) Release of prostaglandin D2 by Murine Mast Cells: Importance of Metabolite Formation of Antiproliferative Activity 7: 79-84.*
Hayaishi (1988) Sleep-Wake Regulation by Prostaglandins D2 and E2 JBC 263(29): 14593-14596.*
Shichijo et al (1998) The Effects of Anti-Asthma Drugs on Mediator Release from Cultured Human Mast Cells Clinical and Experimental Allergy 28: 1228-1236.*
Moreadith et al. (1997) Gene Targeting in Embryonic Stem Cells: the New Physiology and Metabolism J Mol Med 75: 208-216.*
Pera et al. (2000) Human Embryonic Stem Cells J of Cell Science 113(5): 5-10.*
Cell, vol. 90, No. 6, pp. 1085-1095 (1997).
Cell, vol. 83, No. 5, pp. 803-812 (1995).
Cell, vol. 83, No. 5, pp. 813-819 (1995).
Proc. Natl. Acad. Sci. USA, vol. 97, No. 9, pp. 4903-4907 (2000).
Saibou Kougaku, vol. 17, No. 5, pp. 707-713 (1998).
Shinyaku to Rinshou, vol. 45, No. 9, pp. 1647-1650 (1996).
Tanpakushitsu, Kakusan, Kouso, vol. 45, No. 6, pp. 1072-1076 (2000).
Isotope News, No. 522, pp. 6-11 (1997).
Masui, vol. 47, special issue, pp. S11-S17 (1998).
Medical Immunology, vol. 15, No. 2, pp. 217-220 (1988).
Tanpakushitsu Kakusan Kouso, vol. 40, No. 14, pp. 2001-2007 (1995).
Bio Science to Industry, vol. 58, No. 9, pp. 643-644 (2000).
Nippon Rinshou, vol. 56, No. 2, pp. 488-492 (1998).

* cited by examiner

*Primary Examiner*—Sumesh Kaushal
*Assistant Examiner*—David A. Montanari
(74) *Attorney, Agent, or Firm*—Wenderoth, Lind & Ponack, L.L.P.

(57) ABSTRACT

The present application provides a human gene over-expressing animal, which is a non-human animal carrying a human hematopoietic prostaglandin $D_2$ synthase gene in its somatic cell chromosome and expressing a large amount of human prostaglandin $D_2$ synthase, wherein the animal is one obtained through ontogenesis of a totipotency cell of a non-human animal or offspring of the obtained animal, and the totipotency cell is introduced with said synthase gene. The present application also provides a method of using the transgenic animal for testing in vivo activity of a candidate for anti-allergy medicines, sleep-controlling substances and candidates for anti-obesity.

4 Claims, 7 Drawing Sheets

10 μg total RNA/lane

ANIMAL WITH THE MASS EXPRESSION OF HUMAN GENE AND TEST METHOD BY USING THE ANIMAL

This is a 371 U.S. National Stage Application of PCT JP00/06963, filed Oct. 5, 2000.

TECHNICAL FIELD

The invention of this application relates to a human gene over-expressing animal, and to various test methods using the animal. More precisely, the invention of this application relates to a non-human transgenic animal which carries, in its somatic cell chromosome, a gene encoding human PGD synthase (H-PGDS), an enzyme for synthesizing prostaglandin $D_2$ ($PGD_2$) that is one causal substance for allergy and sleep induction, and which can produce a large amount of $PGD_2$ through over expression of the enzyme. The invention also relates to methods of using the animal for testing active ingredients of medicines for preventing and curing allergic diseases, sleep disorders, life habit-caused disorders such as obesity.

BACKGROUND ART

H-PGDS (Biochem. Biophys. Acta 575:43–51, 1979; J. Biol. Chem. 262:3820–3825, 1987; Cell 90;1085–1095, 1997) is an enzyme having the function of producing an endogenous substance, prostaglandin $D_2$ ($PGD_2$: Prostaglandins Leukot. Essent. Fatty Acids, 37:219–234, 1989; FASEB J. 5:2575–2581, 1991; J. Lipid Mediat. Cell Signaling, 14:71–82, 1996) that has various physiological activities, and it is expressed in immunocytes and genital organs (J. Immunol. 143:2982–2989, 1989; J. biol. Chem. 270: 3239–3246, 1995). It is known that $PGD_2$ produced from mast cells by the action of H-PADS is involved in excacerbation of inflammations, and its degraded substance, 15d-$PGJ_2$ (15-deoxy-$\Delta$12,14-$PGJ_2$) is a differentiation factor for adipose cell (Cell, 83:803–812 & 813–819, 1995).

H-PGDS is expressed in mast cell and antigen-presenting cell J. Immunol. 143:2982–2989, 1989; J. Biol. Chem. 270:3239–3246, 1995), and participates in production of $PGD_2$ in allergic inflammation. It is known that thus produced $PGD_2$ causes bronchoconstriction and vasodilation and involves in ingravescence of allergies.

Of all endogenous sleep-inducing substances that have been clarified up to the present, $PGD_2$ has the most potent sleep-inducing activity. It is reported that in human patients suffering from trypanosome-infected African sleeping sickness, the $PGD_2$ level in the cerebrospinal fluid increases 100 to 1,000-fold with ingravescence of the disease condition (Trans Royal Soc. Trop. Med. Hyg. 84:795–799, 1990). In addition, it is known that in pathologic deep sleep observed in systemic mastocytosis patients, the blood $PGD_2$ level also increases 150-fold (New Engl. J. Med. 303:1400–1404, 1980), and the important role of $PGD_2$ in pathologic sleep is suggested.

As mentioned above, it is suggested that $PGD_2$ and H-PGDS producing $PGD_2$ closely correlate to various physiological functions of individuals, and may be a potential cause of human diseases. However, no animal model system has as yet been established that enables the study under the controlled condition how the over expression of H-PGDS will act on animal.

The invention of this application has been made in consideration of the above-mentioned situation, and its object is to provide a non-human animal that genetically expresses a large amount of H-PGDS. Another object of this application is to provide methods of using the animal for testing the effectiveness of preventing or curing substances for various diseases caused by the over expression of H-PGDS in the animal.

DISCLOSURE OF THE INVENTION

This application provides inventions of the following (1) to (5):

(1) A human gene over-expressing animal, which is a non-human animal carrying a human hematopoietic prostaglandin $D_2$ synthase gene in its somatic cell chromosome and expressing a large amount of human prostaglandin $D_2$ synthase, wherein the animal is one obtained through ontogenesis of a totipotency cell of a non-human animal or offspring of the obtained animal, and the totipotency cell is introduced with said synthase gene.

(2) The human gene over-expressing animal of the invention (1), wherein the non-human animal is a mouse.

(3) A method for testing in vivo activity of a candidate for the anti-allergy medicines, which comprises administering the candidate to the human gene over-expressing animal of the invention (1) or (2), and measuring allergic reactions of the animal to thereby evaluate the activity of the candidate.

(4) A method for testing in vivo activity of sleep-controlling substances, which comprises administering a candidate for the substances to the human gene over-expressing animal of the invention (1) or (2), and measuring sleep condition of the animal to thereby evaluate the activity of the candidate.

(5) A method for testing in vivo activity of a differentiation-controlling substance for mast cell and adipose cell, which comprises administering a candidate for the substance to the human gene over-expressing animal of the invention (1) or (2), and measuring the obesity condition of the animal to thereby evaluate the activity of the candidate.

THE REST MODE FOR CARRYING OUT THE INVENTION

Figure 1:
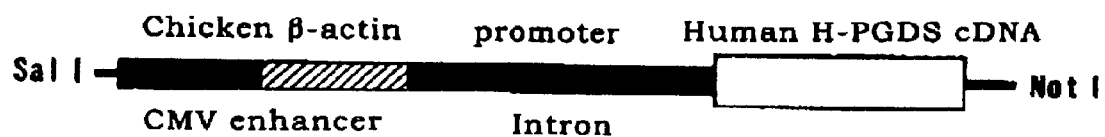
FIG. 1 is a schematic view showing the construction of the transfer vector used in producing a transgenic mouse of this invention.

For the transgene, human H-PGDS gene, its cDNA can be used. The H-PGDS cDNA may be prepared according to a method that comprises synthesizing an oligonucleotide based on the base sequence of a desired part of a known rat cDNA sequence (Cell 90:1085–1095, 1997; GenBank Accession No. D82071) or human cDNA sequence (Eur. J. Biochem. 267:3315–3322, 2000; GenBank Accession No. NM014485), and using it as a probe to screen a human cDNA library, or an RT-PCR method that comprises synthesizing oligonucleotides capable of hybridizing sequences at both ends of the intended cDNA fragment, and using it as primers to prepare the H-PGDS cDNA from an mRNA isolated from human cells.

The transgene has a promoter sequence or an enhancer sequence linked thereto, which is for controlling the over expression of the gene. The promoter sequence or the enhancer sequence are not specifically defined, for which, for example, suitably used is a promoter region or an enhancer region of a gene capable of being highly expressed in various organs of the transgenic animal.

The human gene over-expressing animal of the invention (1) can be produced in accordance with a known method of producing transgenic animals (for example, Proc. Natl. Acad. Sci. USA 77:7380–7384, 1980). Specifically, the transgene is introduced into totipotency cell of a non-human animal, the cell is ontogenized into individuals, and those carrying the transgene in the genome of the somatic cells thereof are selected. The thus-selected individuals are of the intended transgenic animal. From the technical viewpoint, animals of any and every species may be employed for the non-human animal for use herein, but mice are the best for it, since a large number of inbred lines have been available and, in addition, the technique of fertilized egg incubation and external fertilization thereof has been established in the art. Of mice, the totipotency cell to be introduced with the gene may be those of fertilized eggs or early embryos. For gene introduction into cultured cell, DNA microinjection method is the best in view of the yield of the transgenic animals and of the transgene transfer efficiency to the next generations.

The fertilized eggs into which the gene has been injected are implanted into the oviduct of a surrogate mother, in which the eggs are ontogenized into an individuals, and the individual animals are born from it and then are bred by a foster mother. Thus bred, DNA is extracted out of the animal at a part of its body (the tip of the tail), and subjected to Southern blotting analysis or PCR to corm the presence of the transgene. The individual animal in which the presence of the transgene has been confirmed is the founder, and the transgene is transferred to 50% of the offspring of the founder. In that manner, wild-type or variant animals can be produced efficiently.

The thus-produced transgenic animal produces excess H-PGDS, and therefore can be the best model for investigating the physiological activities of $PGD_2$.

The invention (3) of this application is a method for testing in vivo activity of a candidate for anti-allergy medicines, which comprises administering the candidate to the human gene over-expressing animal of the invention (1), and measuring the allergic reaction in the animal to thereby evaluate the activity of the candidate. Specifically, the transgenic animal of the invention (1) carries a large amount of H-PGDS and produces a large amount of $PGD_2$, and therefore sensitively reacts with various types of allergens. Accordingly, for example, when a certain allergen is previously administered to the animal, a candidate for anti-allergy medicine is then administered thereto, and the systemic allergic reaction of the animal is measured, then the pharmacological activity of the candidate can be evaluated.

The invention (4) of this application is a method for testing in vivo activity of a sleep-controlling substance, which comprises administering a candidate for the substance to the human gene over-expressing animal of the invention (1), and measuring the sleep condition of the animal to thereby evaluate the activity of the candidate. Specifically, the transgenic animal of the invention (1) carries a large amount of H-PODS and produces a large amount of $PGD_2$, and therefore its sleep control is disordered due to the strong sleep-inducing action of $PGD_2$. Accordingly, for example, when a candidate for sleep control (for example, a substance having the ability to sustain vigilance) is administered to the animal and the awake/sleep condition of the animal is measured, and then the pharmacological activity of the candidate can be evaluated. The awake/sleep condition of the animal can be determined by measuring the locomotor activity thereof or measuring the food intake or water intake thereof, or by measuring the physiological parameters such as electroencepharogram or electromyogram thereof.

The invention (5) of this application is a method for testing in vivo activity of a candidate for anti-obesity medicine, which comprises administering a candidate for anti-obesity medicine to the human gene over-expressing animal of above (1), and measuring the degree of obesity of the animal (e.g., body weight, fatty tissue weight) to thereby evaluate the activity of the candidate. Specifically, the transgenic animal of the invention (1) carries a large amount of H-PGDS and produces a large amount of $PGD_2$, and therefore produces a large amount of $15d\text{-}PGJ_2$ that involves in increase of the body weight or fatty tissue weight in the animal, and, as a result, the animal gets fat. Accordingly, for example, when a candidate for anti-obesity is administered to the animal and the degree of the obesity of the animal is measured, and then the pharmacological activity of the candidate can be evaluated.

EXAMPLES

The invention of this application is described in more detail and concretely with reference to the following Examples, which, however, are not intended to restrict the scope of the invention of this application.

Example 1

(1) Production of Transgenic Mice:

From the cDNA library prepared from mRNA of human cells, human H-PODS cDNA was cloned by using rat H-PGDS cDNA as a probe.

Next, the human H-PGDS cDNA was inserted and linked into a cloning site (SalI/NotI) of the vector (pCAGGS) to construct a transfer vector. FIG. 1 shows the construction of the transgene in the transfer vector. As in FIG. 1, the transgene has a CMV enhancer and a chicken β-actin promoter upstream the H-PGDS cDNA, and when introduced into a mouse chromosome, it expresses a large amount of H-PGDS mRNA owing to the action of the enhancer and the promoter.

The transfer vector was introduced into fertilized eggs of an FVB mouse through microinjection. The gene-introduced fertilized eggs were then implanted into the oviduct of a surrogate mother in an ordinary manner, in which those are ontogenized into individuals, and the individuals were then born.

Figure 2:
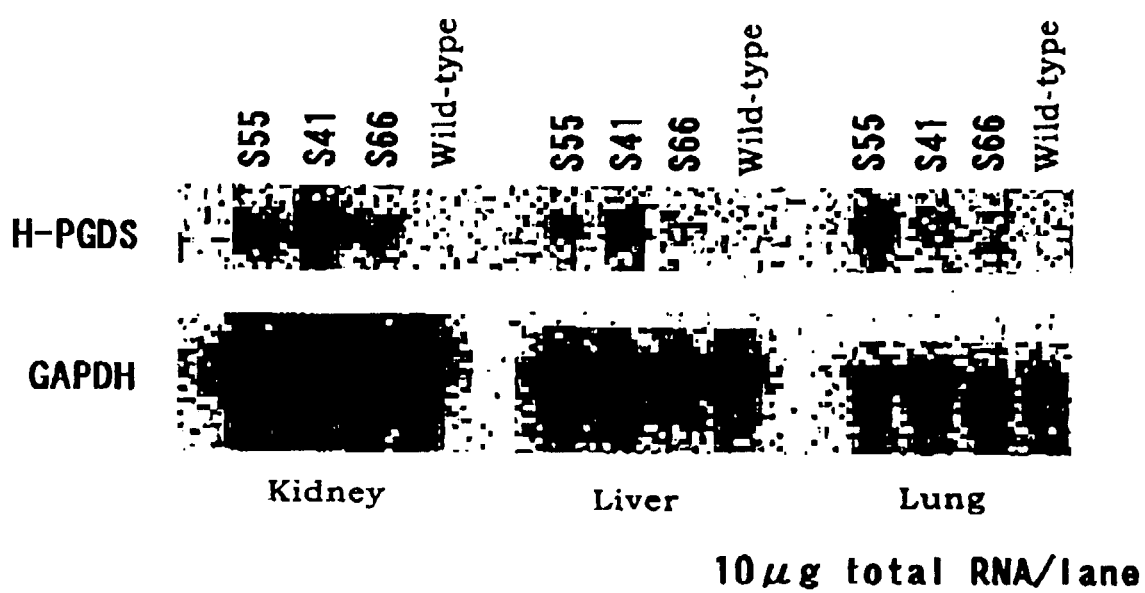
FIG. 2 shows the results of H-PGDS Northern blot analysis of mRNA extracted from various organs of three lines of transgenic mice and from those of a wild-type mouse.

DNA was extracted from the tail of each of the thus-obtained mouse individuals, and it was analyzed through Southern blotting analysis using a probe that had been synthesized on the basis of the sequence of the transgene. Based on the data of the thus-analyzed DNA, transgenic mice were selected. Three independent lines of transgenic mice were thus established, which differ from each other in the degree of H-PGDS expression therein. The data are as in FIG. 2.

Figure 3:
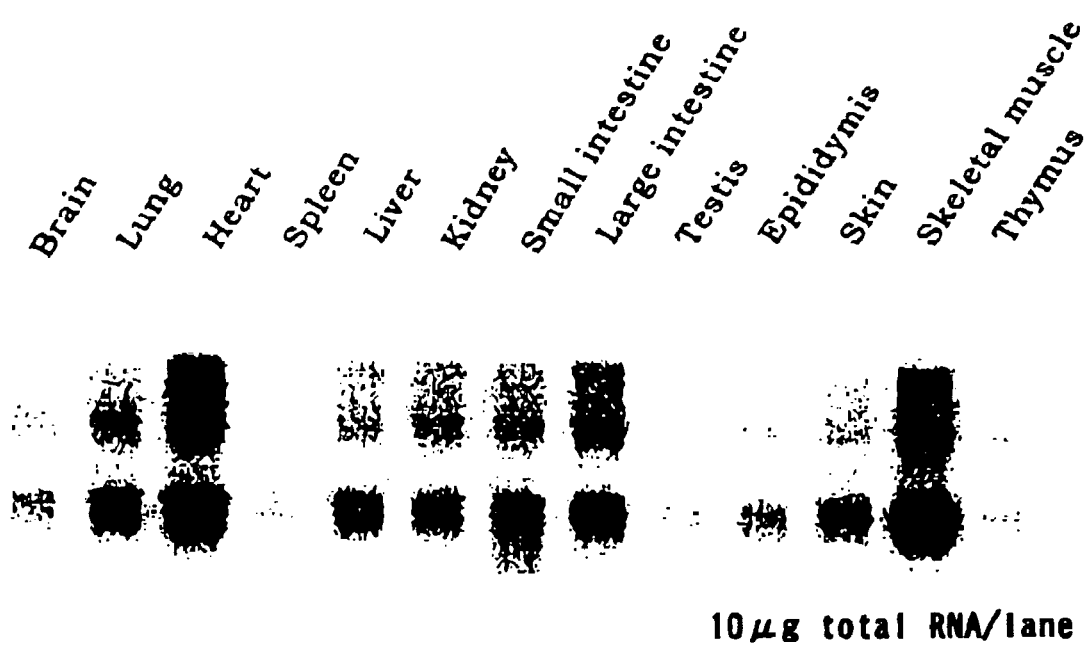
FIG. 3 shows the results of H-PGDS Northern blot analysis of mRNA extracted from all organs of a transgenic mouse.

(2) Investigation of Gene Expression in Transgenic Mice:

Systemic expressions of the transgene of the transgenic mice were examined with Northern blot analysis. As a result, it was confirmed that in S55 mouse, the H-PGDS gene was expressed to a high level in the skeletal muscle, the heart, the lung, the large intestine and the liver. The data are as in FIG. 3.

Figure 4:
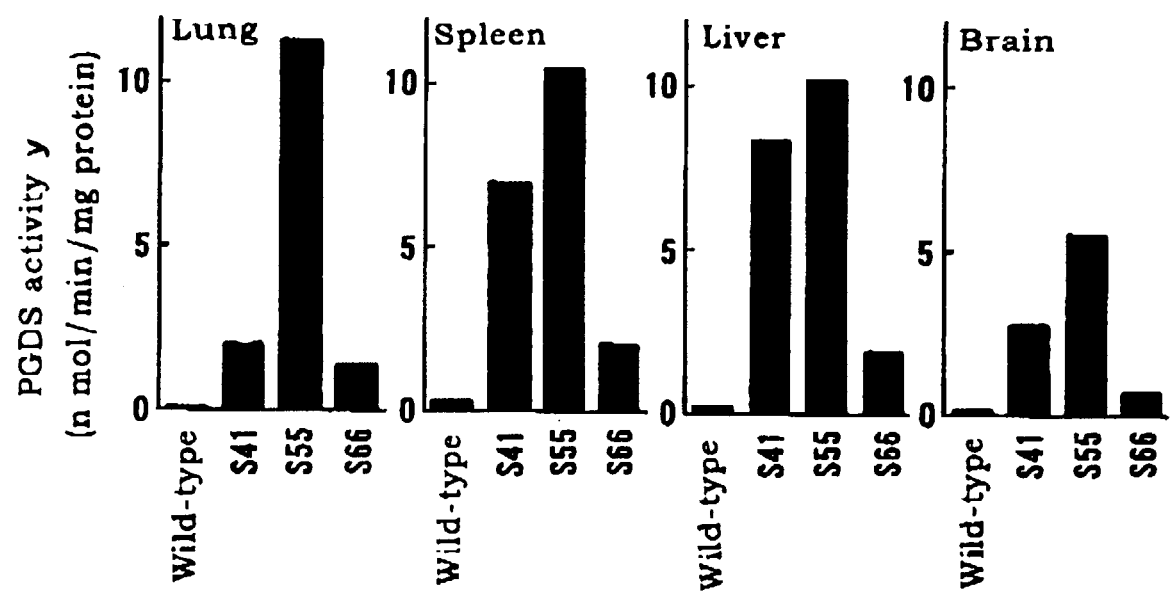
FIG. 4 shows the results of H-PGDS enzyme activity data obtained by using fractionations of proteins extracted from various organs of three lines of transgenic mice and from those of a wild-type mouse.

(3) Investigation of POD Enzyme Activity in Transgenic Mice:

Using a substrate $PGH_2$, the POD enzyme activity in various organs of the transgenic mice was determined. In the transgenic mice, the enzyme activity significantly increased in various organs. The three lines of transgenic mice were compared with each other in point of the enzyme activity thereof. The enzyme activity increase in these was in an order of S55>S41>S66. The data are as in FIG. 4.

Example 2

As a human asthma model, the transgenic mice obtained in Example 1 were analyzed in antigen-induced lung inflammation model.

Figure 5:
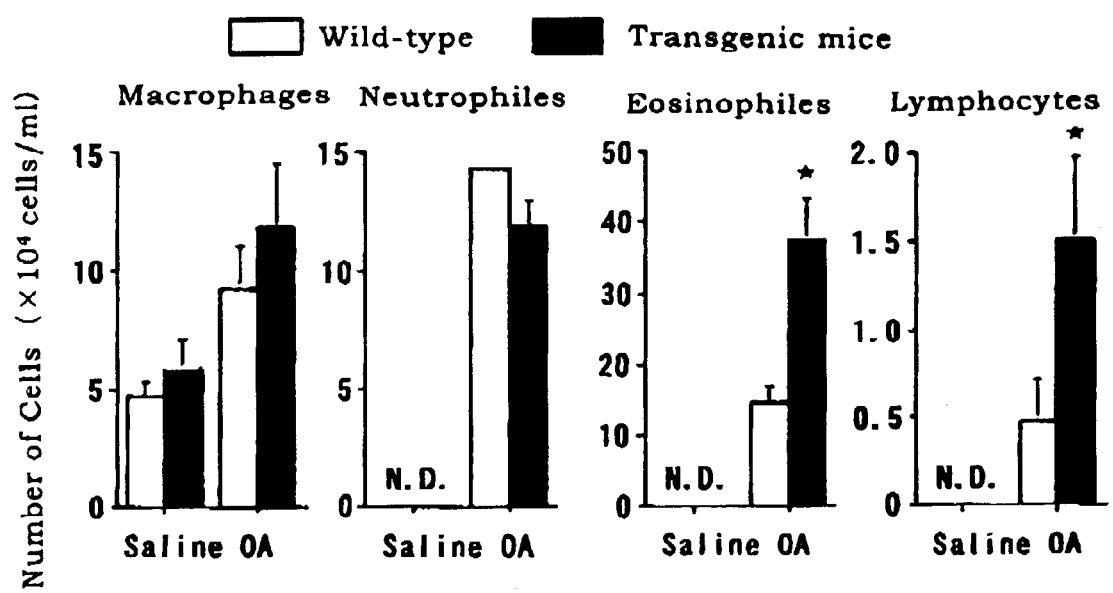
FIG. 5 shows the data of inflammatory cells counted in the wash of air vesicles of antigen-immunized transgenic mice and wild-type mice after exposure to physiological saline or antigen.

After antigen challenge, the invasion of eosinophilic leukocytes into the lung of the transgenic mice significantly increased, as compared with that into the lung of the wild-type mice. The data are as in FIG. 5.

The result as above confirms that the transgenic mice of this invention are useful as a model animal for clarifying the mechanism of allergosis and are effective for the system of screening novel anti-allergy substances.

Example 3

A lipopolysaccharide was intraperitoneally administered to the transgenic mice obtained in Example 1, and the inflamed mice in narcolepsy were analyzed.

Figure 6:
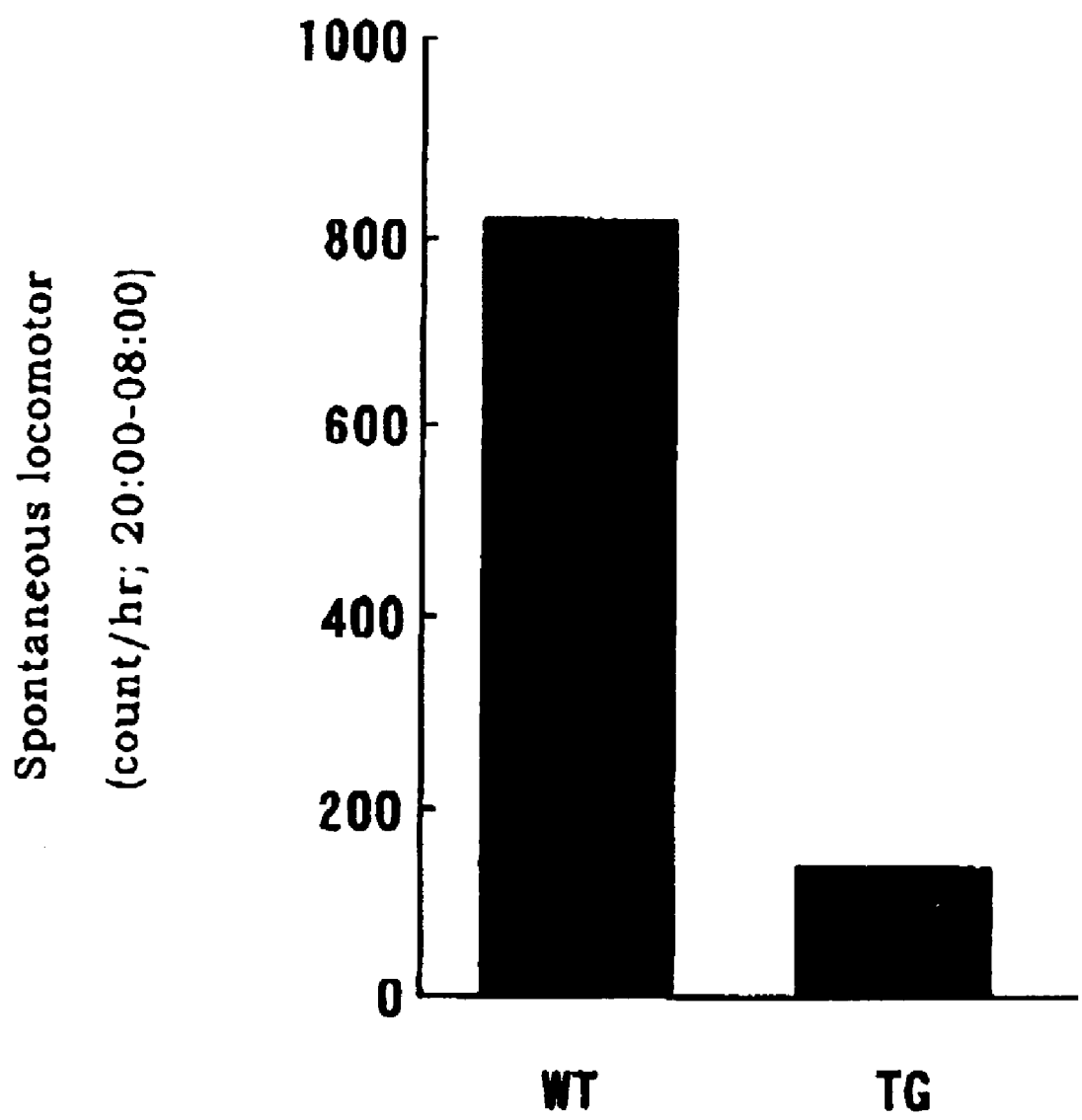
FIG. 6 shows the data of spontaneous locomotor for 12-hours of transgenic and wild-type mice with intraperitoneal administration of lipopolysaccharide (20 mg/kg).

Concretely, a high-concentration (20 mg/kg) lipopolysaccharide was administered to the transgenic mice, and the spontaneous locomotor of each mouse was observed. As a result, the spontaneous locomotor of the transgenic mice significantly lowered as compared with that of the wild-type mice. This suggests that the sleep time of the transgenic mice increased. The data are as in FIG. 6.

The result as above confirms that the transgenic mice of this invention are useful as a model animal for clarifying the mechanism of sleep induction and are effective for the system of screening novel substances of controlling sleep-awake rhythm.

Example 4

The transgenic mice obtained in Example 1 and wild-type mice were loaded with a high-fat food, and analyzed for the obesity progress.

Figure 7:
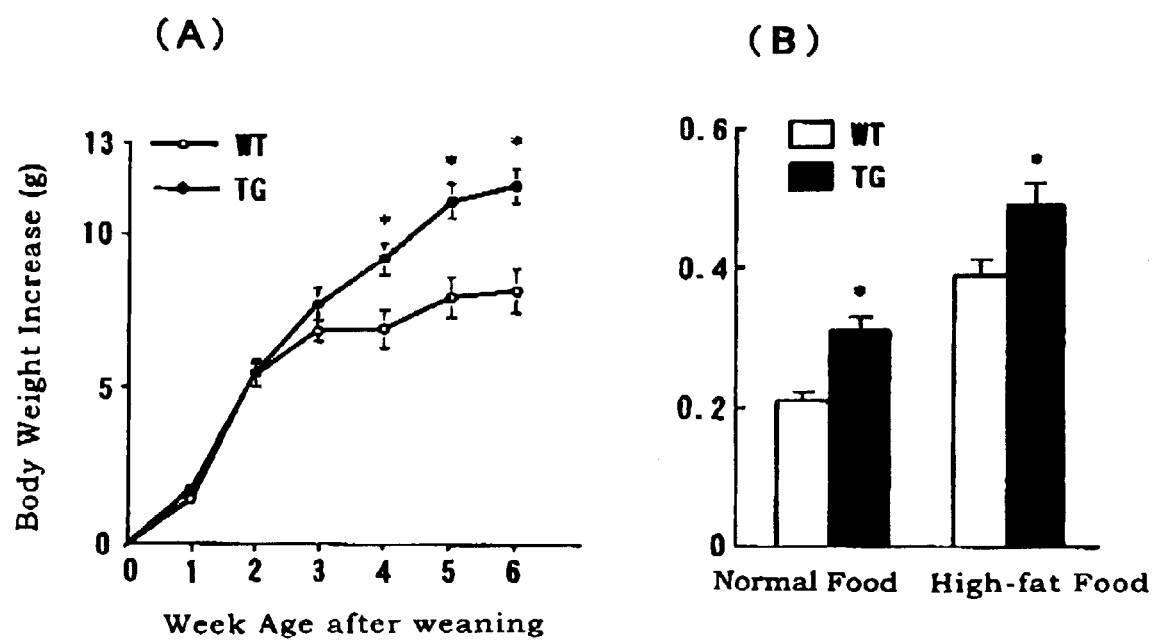
FIG. 7 shows the data (A) of body weight change of transgenic (TG) and wild-type (WT) mice fed with a high-fat food, and the data (B) of white adipose tissue weight of the mice fed with a normal food or a high-fat food.

Concretely, the mice were loaded with a high-fat food for 6 weeks, and their body weight increase was observed. As compared with that of the wild-type mice, the body weight of the transgenic mice significantly increased. In addition, the white adipose tissue weight of the transgenic mice also significantly increased. The data are as in FIG. 7.

INDUSTRIAL APPLICABILITY

As described in detail hereinabove, the invention provides a transgenic animal that expresses a large amount of H-PODS and therefore produces a large amount of $PGD_2$. The animal promotes the development of medicines for various human diseases.

The invention claimed is:

1. A transgenic mouse whose genome encodes a transgene comprising a human prostaglandin D2 synthase gene, wherein overexpression of the human prostaglandin D2 synthase gene results in an increase of human hematopoietic prostaglandin D2 synthase in the lung, spleen, and liver at a level more than 5 times that of a wild-type mouse.

2. A method for testing the in vivo activity of a candidate anti-allergy substance, said method comprising administering said candidate substance to the transgenic mouse of claim 1, and measuring allergic reactions in said transgenic mouse to evaluate the activity of said candidate substance.

3. A method for testing the in vivo activity of a candidate substance that affects sleep-awake rhythm, said method comprising administering said candidate substance to the transgenic mouse of claim 1, and measuring the sleep time in said transgenic mouse to evaluate the activity of said candidate substance.

4. A method for testing the in vivo activity of a candidate weight-lowering substance that affects obesity, said method comprising administering said candidate substance to the transgenic mouse of claim 1, and measuring the weight of said transgenic mouse to evaluate the activity of said candidate substance.

* * * * *